United States Patent [19]

Quilichini

[11] 4,000,265
[45] Dec. 28, 1976

[54] METHOD FOR TREATING ARTERIOSCLEROTIC AND CARDIOVASCULAR DISORDERS

[75] Inventor: Raymond Quilichini, Bordeaux, France

[73] Assignee: Societe Cortial, Paris, France

[22] Filed: Sept. 10, 1975

[21] Appl. No.: 611,847

[30] Foreign Application Priority Data

Sept. 10, 1974 France .......................... 74.31435
Apr. 21, 1975 France .......................... 75.13152

[52] U.S. Cl. .............................................. 424/184
[51] Int. Cl.² ....................................... A61K 31/695
[58] Field of Search ................................. 424/184

[56] References Cited
UNITED STATES PATENTS 3,558,683  1/1971  Belsky et al. ..................... 424/184
3,651,115  3/1972  Belsky et al. ..................... 424/184

*Primary Examiner*—Donald R. Moyer
*Attorney, Agent, or Firm*—Oblon, Fisher, Spivak, McClelland & Maier

[57] ABSTRACT

A pharmaceutical composition comprising an active silicon containing compound of the formula:

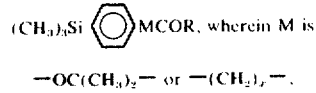

$(CH_3)_3Si$—⟨⟩—MCOR, wherein M is $-OC(CH_3)_2-$ or $-(CH_2)_x-$.

wherein $x$ is 0 or an integer of 1 – 3, and R is OH, alkoxy or amidoalkoxy. The composition is useful for the treatment of arteriosclerotic and cardiovascular disorders.

11 Claims, No Drawings

METHOD FOR TREATING ARTERIOSCLEROTIC AND CARDIOVASCULAR DISORDERS

BACKGROUND OF THE INVENTION

1. Field of the Invention:

The present invention relates to a pharmaceutical composition containing an organosilicon compound as the active agent. More particularly, the present invention relates to an organosilicon containing composition for the treatment of cardiovascular and arteriosclerotic disorders.

2. Description of the Prior Art:

It is well known that silicon plays an essential role in metabolic processes and particularly in processes which occur at the level of connective and epithelial tissues. J. Loeper et al, *Presse Medicale*, 74, 17, 865–8 (1966), have shown that the silicon content at the level of the aorta decreases very rapidly with age, and that this decrease, moreover, is associated with the appearance of atheromatous lesions.

The first uses of silicon, in the form of mineral compounds, date from the beginning of the century (A. Gouget, *Presse Medicale*, 1910, 6, 27). These attempts were disappointing since these mineral compounds are insoluble in water or release, on contact with the gastric juice, an insoluble silicic acid which is difficult for the system to assimilate (M. C. Voroijkov, *Pure and Applied Chem.*, 1968, 17, 399).

More recent studies, using organic compounds of silicon containing the component Si—O—, such as the complex monomethylsilanetriolsodiumorthohydroxybenzoate (J. Loeper et al, *Arch. Mal. due Coeur*, 1968, 61, suppl. 1, 78 – 80), have shown that these compounds have a preventive and curative effect vis a vis atheromatosis when they are administered intravenously. Taken orally, these products have no effect.

A need therefore, continues to exist for silicon containing compositions which can be administered orally to effectively treat cardiovascular and arteriosclerotic disorders.

SUMMARY OF THE INVENTION

Accordingly, one object of the present invention is to provide a silicon containing composition which is effective in the treatment of cardiovascular and arteriosclerotic disorders.

Another object of the present invention is to provide compositions containing a class of silicon compositions which can be administered orally, by injection or in the form of suppositories or gelled capsules.

Briefly, these objects and other objects of the invention as hereinafter will become more readily apparent can be attained by a pharmaceutical composition containing a silicon compound with the structural element Si—C and having the formula:

wherein M represents —OC(CH$_3$)$_2$— or —(CH$_2$)$_x$—, wherein $x$ is 0 or an integer from 1 – 3 and R is OH, alkoxy or amidoalkoxy.

DETAILED DESCRIPTION OF THE PREFERRED EMBODIMENTS

The silicon containing compounds which are the essential components of the pharmaceutical compositions of the present invention can be synthesized by any one of a number of conventional synthetic procedures. A non-limiting representative example of a suitable procedure is a two-step preparation of p-(trimethylsilyl)benzoic acid, wherein the first step is described H. Freiser et al, *J. Am. Chem. Soc.*, 75, 2821–2822 (1953), and the second step is described by Tzu-Shen-Lin, et al, Hua Hsuch Pao, 26, 7 – 10 (Chem. Abstracts, 55, 18654a (1961)). Both steps of the procedure are shown in the following reaction sequence.

Another non-limiting example is the preparation of p-trimethyl-silylphenoxyisobutyric acid wherein the first step of the synthetic procedure involves the preparation of p-trimethylsilylphenol. Thereafter, the p-trimethylsilylphenol is condensed with acetone in a basic chloroform medium to form the desired p-trimethylsilylphenoxyisobutyric acid product.

The active silicon compounds of the present invention are characterized by the structural element Si—C and have the formula:

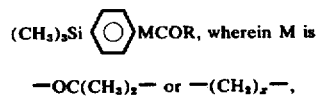

wherein $x$ is 0 or an integer from 1 – 3, and R is OH, alkoxy or amidoalkoxy. Preferably, the alkoxy groups contain from one to six carbon atoms. Of the amidoalkoxy compounds, hydroxy 4-N-dimethylbutyramido-p-trimethylsilylphenoxyisobutyrate and hydroxy 4-N-dimethylbutyramido p-trimethylsilylbenzoate are preferred.

Alkali metal salts of the silyl acids can be prepared as well as salts of the silyl acids with organic bases such as lysine. The salts are very stable in aqueous solutions and can be stabilixed without decomposition in the autoclave at 120° C. The pharmaceutical compositions of the present invention involve the combination of a silicon compound of the invention with a suitable liquid or solid pharmaceutical carrier. Thus, the present composition can be formulated as a suppository, gelled capsules or other gelled forms, or as an injectable or drinkable solution. The silyl compounds are perfectly soluble in water and do not decompose at high temperatures. In order to make the gelled capsules, a silyl compound is used in such a way as in a distilled water solution and in compressed or tablet form with the usual compression excipients such as fillers or carriers, sweetening agents and flavoring agents.

Aqueous solutions of the silicon compounds can be prepared with sodium hydroxide in concentrations between 0.1 and 10%. The solutions are perfectly stable and sterilizable without decomposition in the autoclave at 120° C. When the concentration of the silicon compound approaches 1.5% by weight of the active compound, their cryoscopic depression is of the order of −0.56° C, which authenticates the isotonic character of the compounds toward blood plasma.

The pharmaceutical composition of the present invention is effective in such host animals as the higher mammals including man.

Having generally described this invention, a further understanding can be obtained by reference to certain specific examples which are provided herein for purposes of illustration only and are not intended to be limiting unless otherwise specified.

EXAMPLE 1

Synthesis of p-trimethylsilylphenoxyisobutyric acid

In the first step of the reaction p-trimethylsilylphenol was synthesized by the procedure of J. L. Speier in *J. Am. Chem. Soc.*, 74, 1003 – 1010 (1952). Thereafter, the desired product was synthesized by reacting 26 g of p-trimethylsilylphenol, 200 ml of acetone and 36 g of caustic soda at reflux temperature. A further 24 g amount of chloroform was added and refluxing was continued for an additional three hours. Thereafter, excess acetone was removed by distillation, and the residue was dissolved in water and extracted with diethyl ether. The aqueous solution was acidified with dilute sulfuric acid and extracted again with ethyl ether. The ether extracts were washed until the aqueous extract was neutral, and then the ether solution was dried over anhydrous sodium sulfate and distilled. A crystalline material was obtained. The crystalline material was washed with a few milliliters of cold hexane and dried whereby very lightly yellow colored crystals of p-trimethylsilylphenoxyisobutyric acid having a melting point of 92° – 93° C were obtained. An analysis of the product indicated a silicon content of 11.1% silicon. The product is soluble in ether, benzene, chloroform and acetone and less soluble in hexane and petroleum ether.

Alkoxy and alkoxyamide derivatives of the various silyl acids of the invention can readily be prepared by first converting the acid to the corresponding acid halide, and then reacting the acid chloride with an appropriate alcohol.

EXAMPLE 2

Synthesis of p-(trimethylsilyl)benzoic acid

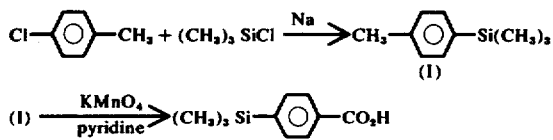

The silyl substituted benzoic acid compound obtained is a white crystalline solid having a melting point of 116° – 118° C, and is soluble in most organic solvents. It can be recrystallized from hexane or petroleum ether, and it is very slightly soluble in water. The compound was analyzed and found to have a silicon content of 14.45%.

Experiments on the acute and chronic toxicity of the present silicon compounds have been performed on different types of animals, notably on the mouse "Swiss", the white rat "Wistar" and the rabbit "Fauve de Bourgogne". In the acute phase, the administration by mouth of a dose of 1 g/kg in all of the test animals caused no mortality nor any change in behavior. Moreover, the intravenous or intramuscular injection of a dose of 400 mg/kg caused no mortality.

In the chronic phase over a period of 3 months, the daily administration of a dose equal respectively to 1/10 orally and 1/50 intravenously or intramuscularly produced no significant modification of the growth curve nor visible effect on the behavior of the animals.

Anatomo-pathologic examination of the viscera of the tested animals both in the acute and in the chronic phase showed no alteration of the tissues. These results have been confirmed by electron-microscopic examination of the cellular infrastructures.

These products possess remarkable anti-arteriosclerosis properties.

EXAMPLE 3

Tests were conducted on 75 rabbits divided into five groups:
  Group 1: healthy subjects
  Group 2: arteriosclerotic subjects
  Group 3: subjects treated intravenously with the dose of 10 mg/kg every second day
  Group 4: subjects treated intravenously with the dose of 4 mg/kg every second day
  Group 5: subjects treated orally with the dose of 10 mg/kg every other day Groups 2, 3, 4 and 5 followed a diet with a cholesterol base (2 g/day).

After 3 months on an atherogenic diet and treatment of Groups 3, 4 and 5 it could be determined that the growth curve was normal. In all the subjects, macroscopic and microscopic study of the principal viscera showed no pathologic structure with the exception of the liver which showed varying degrees of steatosis.

In the animals of arteriosclerotic Group 2, the vascular walls, at the level of the coronaries, the aorta and its branches were entirely coated with lipidic plagues and fibers partially obstructing the arteries. The arteriosclerotic subjects treated intravenously exhibited only excess liquid plagues essentially at the bifurcations. In the arteriosclerotic subjects treated orally, the vascular wall exhibited only a few plagues of excess lipid in the entire group and in some cases even showed a structure identical to that of the healthy subjects.

These anatomo-pathologic results have been verified by an electron-microscopic study. This study effectively establishes the remarkable powers of these organo-silicic compounds for protecting and regenerating vascular wall structures and shows them to be major therapeutic agents for cardiovascular and arteriosclerotic disorders. It has also been found that these compounds possess remarkable efficacy in hyperchlolesterolemia and hyperlipemia.

EXAMPLE 4

The tests were performed using adult "Wistar" rats of average weight 250 g. The male rat was selected in order to avoid modifications of the serous lipids caused, in the female, by the estrous cycle. The blood samples were taken from the tail 24 hours and 7 days after the daily ingestion of the products. These tests were carried out in comparison with clofibrate, the effectiveness of which in hypercholesterolemia and hyperlipemia has been duly established.

In a first series, the doses employed in a single administration were 50 mg and 300 mg/kg for the compounds A, B and D and clofibrate and 50 mg and 200 mg/kg for compound C. The dose was administered by mouth, using an esophageal probe, the animal having fasted, and the blood samples were taken 24 hours later. The experiment included a total of 11 groups of 15 male rats of which one was a control group.

In a second series, the daily doses administered over 7 days were 100 mg/kg for the compounds A and D and clofibrate, the blood samples being taken 24 hours after the last administration. The experiment included a total of 4 groups of male rats, one of which was a control group. The results obtained are summarized in the following table. In the Table, compounds A, B, C and D are p-trimethylsilylbenzoic acid, ethyl p-trimethylsilylbenzoate, hydroxy 4-N-dimethylbutyramido p-trimethylsilylbenzoate and p-trimethylsilylphenoxyisobutyric acid respectively.

| | | Effects on Hyperlipemia Compared In The Adult Male Rat | | | | | |
|---|---|---|---|---|---|---|---|
| | | PERCENTAGE OF REDUCTION | | | | | |
| | | Cholesterolemia | | Total Lipids | | Triglycerides | |
| | | after single dose | after 7 days | after single dose | after 7 days | after single dose | after 7 days |
| Control animals | | 0 | 0 | 0 | 0 | 0 | 0 |
| Clofibrate | 50mg/kg | 3.6 | — | 2.5 | — | 13.3 | — |
| Clofibrate | 100mg/kg | — | 16.5 | — | 29.5 | — | 32.3 |
| Clofibrate | 300mg/kg | 44.4 | — | 47.2 | — | 42.8 | — |
| Compound A | 50mg/kg | 24.0 | — | 18.6 | — | 39.0 | — |
| Compound A | 100mg/kg | — | 11.7 | — | 55.8 | — | 58.4 |
| Compound A | 300mg/kg | 78.8 | — | 70.3 | — | 74.4 | — |
| Compound B | 50mg/kg | 21.7 | — | 17.1 | — | 37.1 | — |
| Compound B | 300mg/kg | 68.9 | — | 59.8 | — | 70.0 | — |
| Compound C | 50mg/kg | 17.8 | — | 21.0 | — | 20.9 | — |
| Compound C | 200mg/kg | 10.7 | — | 42.3 | — | 50.1 | — |
| Compound D | 50mg/kg | 14.9 | — | 18.1 | — | 17.2 | — |
| Compound D | 100mg/kg | — | 36.3 | — | 39.7 | — | 34.7 |
| Compound D | 300mg/kg | 61.6 | — | 77.1 | — | 63.4 | — |

Each unit for administration of the different galenical forms is dosed with a view to the therapeutic usage with a weight of active substance between 1 mg and 1000 mg.

The following galenical forms of the present composition are only shown for purposes of illustration, and the scope of the invention should not be considered to be limited only to these examples.

EXAMPLE 5

Injectable ampules of 10 ml of a 1.5% aqueous solution of the sodium salt of the organo-silicic compound, used at the rate of one ampule per day in the adult by intravenous injection.

EXAMPLE 6

Potable ampules with 10 ml of a 2.5% aqueous solution of the sodium salt of the organo-silicic compound, at the rate of one or two ampules per day per adult.

EXAMPLE 7

Gelules dosed with 75 mg of active principle with calcium sulfate as the vehicle and magnesium stearate as the lubricant at the rate of two to four gelled capsules per 24 hours.

EXAMPLE 8

Suppositories dosed with 50 and 100 mg and with a low melting point, semi-synthetic glyceride vehicle at the rate of one or two suppositories per day.

Having now fully described this invention, it will be apparent to one of ordinary skill in the art that many changes and modifications can be made thereto without departing from the spirit or scope of the invention as set forth herein.

What is claimed as new and intended covered by Letters Patent is:

1. A pharmaceutical composition suitable for protecting and regenerating vascular wall structures in cardiovascular and arteriosclerotic disorders, which comprises a compound of the formula

$(CH_3)_3Si$⟨O⟩$MCOR$ wherein M is $-OC(CH_3)_2-$ or $-(CH_2)_x-$, wherein $x$ is 0 or an integer of 1–3, and R is OH, alkoxy or amidoalkoxy, wherein said alkoxy group contains from 1–6 carbon atoms, in combination with a pharmaceutically acceptable carrier, wherein said silicon compound is present in said composition in an amount sufficient to protect and regenerate vascular wall structures when the composition is administered to an animal or human in need thereof.

2. The composition of claim 1, wherein the amount of active silicon ingredient in said composition ranges from 1 mg to 1000 mg per unit dosage of said composition.

3. The composition of claim 1, wherein said silicon compound is p-trimethylsilylbenzoic acid.

4. The composition of claim 1, wherein said silicon compound is ethyl p-trimethylsilylbenzoate.

5. The composition of claim 1, wherein said silicon compound is hydroxy 4-N-dimethylbutyramido p-trimethylsilylbenzoate.

6. The composition of claim 1, wherein said silicon compound is p-trimethylsilylphenoxyisobutyric acid.

7. A method for protecting and regenerating vascular wall structures for cardiovascular and arteriosclerotic disorders which comprises administering to an animal or human in need thereof a protective or regenerating effective amount of a compound of the formula:

$-OC(CH_3)_2-$ or $-(CH_2)_x-$, wherein $x$ is 0 or an integer of 1–3, and R is OH, alkoxy or amidoalkoxy, wherein said alkoxy group contains from 1–6 carbon atoms.

8. The method of claim 7, wherein the amount of active silicon ingredient in said composition ranges from 1 mg to 1000 mg per unit dosage of said composition.

9. The method of claim 7, wherein said compound is administered by injection.

10. The method of claim 7, wherein said compound is administered orally in a drinkable solution.

11. The method of claim 7, wherein said compound is administered orally in the form of gelled capsules.

* * * * *